(12) United States Patent
Gysin et al.

(10) Patent No.: US 7,431,936 B2
(45) Date of Patent: Oct. 7, 2008

(54) PROTEINS INVOLVED IN CYTOADHESION OF PLASMODIUM FALCIPARUM RING-STAGE-INFECTED ERYTHROCYTES, ANTIBODIES WHICH BIND TO THE PROTEINS, AND METHODS FOR DETECTING INFECTION, STAGE OF INFECTION AND VACCINES FOR PROTECTING AGAINST INFECTION

(75) Inventors: Juerg Gysin, Saint-Zacharie (FR); Bruno Pouvelle, Saint-Maximin (FR); Artur Scherf, Paris (FR); Pierre Buffet, Paris (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/305,956

(22) Filed: Nov. 29, 2002

(65) Prior Publication Data

US 2004/0018569 A1 Jan. 29, 2004

Related U.S. Application Data

(63) Continuation of application No. PCT/EP01/06874, filed on May 30, 2001.

(60) Provisional application No. 60/207,952, filed on May 31, 2000.

(51) Int. Cl.
- *A61K 39/00* (2006.01)
- *A61K 39/38* (2006.01)
- *A61K 39/015* (2006.01)
- *A61K 38/00* (2006.01)
- *A61K 33/06* (2006.01)
- *A01N 37/18* (2006.01)
- *C07K 17/00* (2006.01)

(52) U.S. Cl. ............... 424/268.1; 424/184.1; 424/265.1; 424/690; 424/266.1; 424/272.1; 424/689; 424/698; 514/2; 514/12; 530/300; 530/305; 530/350

(58) Field of Classification Search ............... 424/184.1, 424/265.1, 266.1, 268.1, 272.1, 698, 690, 424/689; 530/350, 300, 305; 514/2, 12
See application file for complete search history.

(56) References Cited

U.S. PATENT DOCUMENTS

| | | | | |
|---|---|---|---|---|
| 4,767,622 | A * | 8/1988 | Ristic et al. | ............... 424/268.1 |
| 5,192,807 | A | 3/1993 | Gysin et al. | |
| 5,356,927 | A * | 10/1994 | Taraschi et al. | ............. 514/449 |
| 5,573,943 | A | 11/1996 | Saul et al. | |
| 5,631,278 | A * | 5/1997 | Taraschi et al. | ............. 514/449 |
| 6,828,416 | B1 * | 12/2004 | Lal et al. | ..................... 530/300 |
| 6,855,323 | B2 * | 2/2005 | Scherf et al. | ............. 424/272.1 |
| 2002/0055183 | A1 * | 5/2002 | Gysin et al. | ................. 436/512 |
| 2004/0013671 | A1 * | 1/2004 | Gysin et al. | ............... 424/152.1 |
| 2004/0018569 | A1 * | 1/2004 | Gysin et al. | ................. 435/7.22 |
| 2005/0054828 | A1 * | 3/2005 | Gysin et al. | ................... 530/350 |

FOREIGN PATENT DOCUMENTS

| | | | |
|---|---|---|---|
| WO | WO 93/04696 | A1 * | 3/1993 |
| WO | WO 96/30026 | A1 * | 10/1996 |
| WO | WO 01/92321 | A2 * | 12/2001 |
| WO | WO 2004/069874 | A1 * | 8/2004 |

OTHER PUBLICATIONS

Douki et al, Blood, Jun. 2003, 101/12:5025-5032.*
Genton et al, Trends in Parasitology, Jun. 2003, 19/6:264-270.*
Sherman et al, Microbes and Infection, 2003, 5:897-909.*
Hawthrone et al, Molecular and Biochemical Parasitology, 2004, 136:181-189.*
Spielmann et al, Molecular and Biochemical Parasitology, 2000, 111:453-458.*
Ramasamy, BBA, 1998, 1406:10-97.*
Duffy et al, Trends in Parasitology, Aug. 2001, 17/8:354-356.*
Shi et al, PNAS USA, Feb. 1999, 96:1615-1620.*
Astagneau et al, Acta Tropica, 1994, 57:317-325.*
Pawan et al, Vaccine, 1994, 12/9:819-824.*
Gabriel et al, Molecular and Biochemical Parasitology, 1986, 20:67-75.*
Scherf et al, Cellular Microbiology, 2001, 3/3:125-131.*
Kurtis et al, Trends in Parasitology, May 2001, 17/5:219-223.*
Joshi et al, Infection and Immunity, Jan. 2000, 68/1:141-150.*
Kurtis et al, Infection and Immunity, Jul. 1999, 67/7:3424-3429.*
Cox, Nature, Dec. 3, 1992, 360:417-418.*
Taylor-Robinson et al, J. Protozool. Res., 2001, 11:1-18.*
Collins et al, Nature, Sep. 1986, 323:259-262.*
Schneider et al, Molecular and Biochemical Parasitology, 2004, 137:35-41.*
Howard et al, Parasite Immunology, 1986, 8:57-68.*
Douki et al, Blood, Jun. 15, 2003, 101/12:5025-5032.*
Stowers et al, Infection and Immunity, Jun. 1997, 65/6:2329-2338.*
Genton et al, Current Drug Targets—Immune, Endocrine & Metabolic Disorders, 2002, 2:255-267.*
Locher et al, BBA-Protein Structure and Molecular Enzymology, Dec. 1992, 1160/3:275-280 abstract only.*
Baldi et al, EMBO Journal, 2000, 19/11:2435-2443.*
Anders et al, Biochem. Soc. Symp., 1987, 53:103-114.*
Stowers et al, Vaccine96 Cold Spring Harbor Laboratory Press, 1996, pp. 249-253.*
Hughes et al, Molecular and Biochemical Parasitology, 1995, 71:99-113.*

(Continued)

*Primary Examiner*—N. M. Minnifield
(74) *Attorney, Agent, or Firm*—Oblon, Spivak, McClelland, Maier & Neustadt, P.C.

(57) ABSTRACT

The present invention provides the RSP-1 and RSP-2 proteins which are involved in the cytoadhesion of *P. falciparum* during ring-stage infection of erythrocytes, antibodies which bind to the proteins, methods of screening for a *P. falciparum* infection, methods of determining the infective stage of *P. falciparum* and vaccines for protecting individuals from *Plasmodium* sp. infections.

3 Claims, 5 Drawing Sheets

OTHER PUBLICATIONS

Dubois et al, J. Immunological Methods, 1997, 208:29-34.*
Coppel et al, Molecular and Biochemical Parasitology, Dec. 1988, 31/3:223-231 abstract only.*
Howard et al, Molecular and Biochemical Parasitology, 1998, 92:111-122.*
B. Pouvelle, et al., Nature Medicine, vol. 6, No. 11, XP-002199895, pp. 1264-1268, "Cytoadhesion of Plasmodium Falciparum Ring-Stage-Infected Erythrocytes", Nov. 2000.
Y-F. Yang, et al., Molecular and Biochemical Parasitology, vol. 26, No. 1-2, XP-001073690, pp. 61-67, "The Primary Structure of a Plasmodium Falciparum Polypeptide Related to Heat Shock Proteins", 1987.
B. L. Pasloske, et al., Gene, vol. 144, No. 1, XP-002199896, pp. 131-136, "PfEMP3 and HRP1: Co-Expressed Genes Localized to Chromosome 2 of Plasmodium Falciparum", 1994.
S. Uni, et al., American Journal of Tropical Medicine and Hygiene, vol. 36, No. 3, XP-001073686, pp. 481-488, "Ultrastructural Localization of the 150/130 KD Antigens in Sexual and Asexual Blood Stages of Plasmodium Falciparum-Infected Human Erythrocytes", 1987.
U.S. Appl. No. 11/376,124, filed Mar. 16, 2006, Gysin, et al.
Quakyi et al, Infection and Immunity (1989) 57(3), 833-839.
Silva et al, Molecular Microbiology (2005) 56(4), 990-1003.
Culvenor et al, Infection and Immunity (1991) 59(3), 1183-1187.
Jana S. McBride, et al.: "Polymorphism of a High Molecular Weight Schizont Antigen of the Human Malaria Parasite Plasmodium Falciparum": J. Exp. Med., vol. 161, Jan. 1985, pp. 160-180.
Chairat Uthaipibull, et al.: "Inhibitory and Blocking Monoclonal Antibody Epitopes on Merozoite Surface Protein 1 of the Malaria Parasite Plasmodium falciparum": J. Mol. Biol., 2001, pp. 1381-1394.
Ana Szarfman, et al.: "Allelic Forms of gp195, a Major Blood-Stage Antigen of *Plasmodium Falciparum*, are Expressed in Liver Stages": Journal of Experimental Medicine, vol. 167, Jan. 1988, pp. 231-236.

* cited by examiner

PROTEINS INVOLVED IN CYTOADHESION OF PLASMODIUM FALCIPARUM RING-STAGE-INFECTED ERYTHROCYTES, ANTIBODIES WHICH BIND TO THE PROTEINS, AND METHODS FOR DETECTING INFECTION, STAGE OF INFECTION AND VACCINES FOR PROTECTING AGAINST INFECTION

CROSS-REFERENCE TO RELATED APPLICATIONS

The present application is a continuation of PCT/EP01/06874 filed May 30, 2001 and claims the benefit of U.S. provisional application Ser. No. 60/207,952 filed May 31, 2000.

BACKGROUND OF THE INVENTION

1. Field of the Invention

The present invention provides the RSP-1 and RSP-2 proteins which are involved in the cytoadhesion of *P. falciparum* during ring-stage infection of erythrocytes, antibodies which bind to the proteins, methods of screening for a *P. falciparum* infection, methods of determining the infective stage of *P. falciparum* and vaccines for protecting individuals from *Plasmodium* sp. infections.

2. Description of the Background

A common pathological characteristic in *P. falciparum* infection is the cytoadhesion of mature-stage infected erythrocytes (IE) to host endothelium and syncytiotrophoblasts. Massive accumulation of IE in the brain microvascular or placenta is strongly correlated with severe form of malaria[1]. Extensive binding of IE to placental CSA is associated with physiopathology during pregnancy[2,3]. The adhesive phenotype of IE correlates with the appearance of POEMP1 at the erythrocyte surface (approx. 16 hours after merozoite invasion) and therefore only early blood-stage (ring-stage) IE are seen in the peripheral blood. Here we describe results that challenge the existing view of blood-stage IE biology. We demonstrate the specific adhesion of IE, during the early ring-stage, to endothelial cell lines from brain and lung and to placental syncytiotrophoblasts. Later in the blood-stage development of these IE, trophozolites switch to an exclusively chondroitin-sulphate A (CSA) cytoadhesion phenotype. Therefore, adhesion to an individual endothelial cell or syncytiotrophoblast may occur throughout the blood stage cycle, suggesting that there are non-circulating (cryptic) parasite subpopulations in malaria patients. We detected two novel parasite proteins on the surface of ring-stage EI. These proteins disappear shortly after the start of PfEMP1-mediated adhesion. These data have important implications for epidemiological studies, parasite tissue tropism and malarial disease outcome.

SUMMARY OF THE INVENTION

Thus, an object of the present invention is an isolated RSP-1 protein which mediates *Plasmodium falciparum* ring-stage adhesion to endothelial cells and is approximately 200 kilodaltons in size as determined by SDS-polyacrylamide gel electrophoresis.

Another object of the present invention is an isolated RSP-2 protein which mediates *Plasmodium falciparum* ring-stage adhesion to endothelial cells and is approximately 40 kilodaltons in size as determined by SDS-polyacrylamide gel electrophoresis.

Another object of the present invention is an antibody which binds to RSP-1 or RSP-2.

Another object of the present invention is a method of detecting the presence of a Plasmodium species in a sample comprising contacting said sample with the RSP-1 or RSP-2 antibody andidentifying an interaction between the antibody and the Plasmodium species in said sample, wherein said interaction indicates the presence of the Plasmodium species, preferably where the Plasmodium species is *P. falciparum*.

Another object of the present invention is a method of detecting the presence of a Plasmodium antibody in a sample comprising contacting said sample with the isolated RSP-1 or RSP-2 protein; and identifying an interaction between the protein and the Plasmodium antibody in said sample, wherein said interaction indicates the presence of the Plasmodium, preferably where the Plasmodium species is *P. falciparum*.

Another object of the present invention is a method of diagnosing a *Plasmodium falciparum* blood-stage cycle in an individual suspected of being infected with *Plasmodium falciparum* comprising obtaining a biological sample from said individual; contacting said sample with an RSP-1 and/or and RSP-2 antibody; and identifying an interaction between the antibody and an antigen in said sample, wherein said interaction indicates a ring-stage infection.

Another object of the present invention is a method of diagnosing the *Plasmodium falciparum* blood-stage cycle in an individual suspected of being infected with *Plasmodium falciparum* comprising obtaining a biological sample from said individual; contacting said sample with the RSP-1 or RSP-2 protein; and identifying an interaction between the protein and an antibody in said sample, wherein said interaction indicates a ring-stage infection.

Another object of the present invention is an immunogenic composition comprising the isolated RSP-1 and/or RSP-2 protein and a pharmaceutical acceptable carrier and further wherein the immunogenic composition is a vaccine.

Another object of the present invention is a method of protecting an individual against a *Plasmodium falciparum* infection comprising administering RSP-1 and/or RSP-2 to said individual in an amount sufficient to induce an immune response in said individual.

DETAILED DESCRIPTION OF THE INVENTION

Figure 1A:
FIG. 1: Ring-stage $IE^{CSA}$ cytoadhesion to various cells and tissues. $IE^{CSA}$ from highly synchronized cultures cytoadhered to (A) cryosections of liquid nitrogen snap-frozen uninfected human placenta biopsy samples (R, ring- and T, trophozoite stage) or (B) SBEC ID monolayer (Nikon E800, ×1000). (C) Cytoadlesion of synchronized $PA^{CSA}$ IE, at the 8th hour after invasion, to monolayers of SBEC ID, HUVEC, HLEC primo explants, HMEC, C32 and CHO cells and to cryosections of liquid nitrogen snap-frozen uninfected human placenta biopsy samples. After extensive washing, the number of cytoadherent IE per high-power fields of placental cryosections or per mm$^2$ of cell monolayer counted on 4 random fields (0.25 mm$^2$ area at ×300 magnification, Olympus CK2) over the entire surface of each sample was determined. The values for each experiment were standarized to 5% parasitaemia, and the results expresed as a mean cytoadhesion value±SD. (D) Highly synchronized populations of $PA^{CSA}$ and $PA^{CD36}$ IE were mixed at the 8th hours of the cycle to give an initial population, the phenotype distribution of which was determined 24 hours later by cytoadhesion inhibition microassays. The rest of the mixture was immediately subjected to selection by cytoadhesion of SBEC ID. The cytoadherent IE were cultured and the phenotype distribution of the result population determined. The percentage cytoadhesion obtained for each inhibitor. CSA (■) and anti-CD36 FA6-152 monoclonal antibodies ( ) gives the inverse proportion of each phenotype in the IE populations.
Figure 1B:
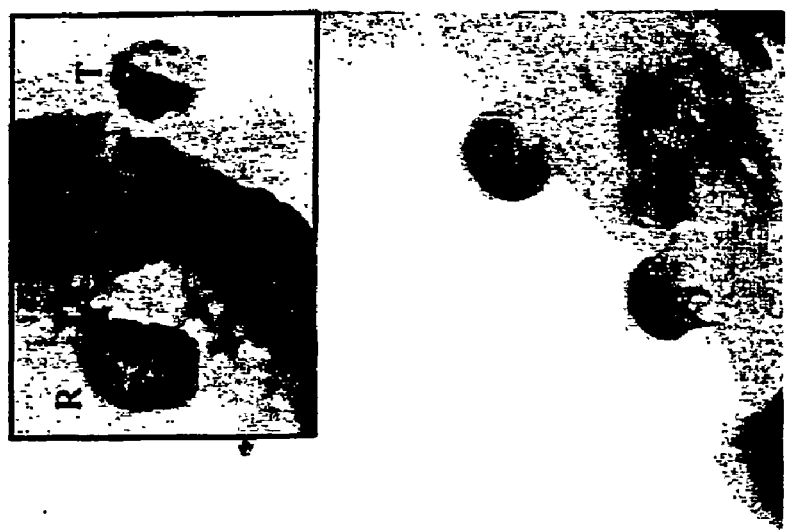

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by vite of prior invention.

The RSP-1 and RSP-2 proteins of this invention may be purified to substantial purity by standard techniques well known in the art, including selective precipitation with such substances as ammonium sulfate, column chromatography, immunopurification methods, and others. See, for instance, R. Scopes, Protein Purification: Principles and Practice, Springer-Verlag: New York (1982).

In addition, provided with the purified proteins of the present invention one of skill in the art will be able to obtain a amino acid sequence from which the polynucleotide sequence which encodes the RSP-1 and RSP-2 proteins can be obtained. Methods for protein sequencing and isolation of a polynucleotide sequence are known in the art and include polynucleotide amplification using primers derived from the amino acid sequence of the purified proteins. These and other methods are disclosed in Current Protocols in Molecular Biology, F. M. Ausebel et al., eds., Current Protocols, a joint venture between Greene Publishing Associates, Inc. and John Wiley & Sons, Inc. (2000) and Maniatis et al. Molecular Cloning: A Laboratory Manual, Cold Spring Harbor Press, 1988.

Having obtained the polynucleotide sequences encoding the RSP-1 and RSP-2 proteins, the polynucleotide sequences can be constructed in recombinant expression vectors for expression of the genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, Guide to Molecular Cloning Techniques, Methods in Enzymology volume 152 Academic Press, Inc., San Diego, Calif. (Berger); and CurTent Protocols in Molecular Biology, F. M. Ausubel et al., eds., Current Protocols, a joint venture between Greene Publishing Associates, Inc. and John Wiley & Sons, Inc., (2000).

Cell cultures that may be used in the present invention, include cell lines and cultured cells from tissue or blood samples is well known in the art. Freshney (Culture of Animal Cells, a Manual of Basic Technique, third edition Wiley-Liss, New York (1994)) and the references cited therein provides a general guide to the culture of cells.

Proteins produced by recombinant DNA technology may be purified by standard techniques well known to those of skill in the art. These proteins can be directly expressed or expressed as a fusion protein. The protein can then be purified by a combination of cell lysis (e.g., sonication) and affinity chromatography. For fusion products, subsequent digestion of the fusion protein with an appropriate proteolytic enzyme releases the RSP-1 or RSP-2 protein sequences.

The proteins of the invention can be used to raise monoclonal antibodies specific for RSP-1 or RSP-2. The antibodies can be used for diagnosis of malarial infection or as therapeutic agents to inhibit binding of merozoites to erythrocytes. The production of monoclonal antibodies against a desired antigen is well known to those of skill in the art. The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and F(ab)$_2$, as well as in single chains.

Antibodies which bind the proteins of the invention may be produced by a variety of means. The production of non-human monoclonal antibodies, e.g., murine, lagomorpha, equine, etc., is well known and may be accomplished by, for example, immunizing the animal with a preparation containing the polypeptide. Antibody-producing cells obtained from the immunized animals are immortalized and screened. Methods of producing polyclonal and monoclonal antibodies are known to those of skill in the art. See, e.g., Coligan (1991) Current Protocols in Immunology Wiley/Greene, N.Y.; and Harlow and Lane (1989) Antibodies: A Laboratory Manual Cold Spring Harbor Press, N.Y. Specific monoclonal and polyclonal antibodies will usually bind with a Kd of at least about 0.1 mM, more usually at least about 1 µM, and most preferably at least about 0.1 µM or better.

The invention relates also to hybridoma and especially to the hybridoma named Pf26G1/B4 deposited at the CNCM (Paris, France) on Feb. 23, 2001 under accession number I-2635.

This hybridoma is specific to chondroitin-sulphate A (CSA) cytoadhesion phenotype. It secretes monoclonal antibodies B4 which react with the native *P. falciparum* proteins at the surface of ring-infected erythrocytes but not with the mature trophozoite and schizonte-infected erythrocytes. B4 inhibits the adhesion of ring-infected erythrocytes and also the re-invasion of the erythrocytes by the merozoites.

The proteins and polynucleotides of the invention can be used in diagnostic applications for the detection of Plasmodium parasites or nucleic acids in a biological sample. The presence of parasites can be detected using several well recognized specific binding assays based on immunological results. For example, labeled antibodies to polypeptides of the invention can be used to detect Plasmodium in a biological sample. Alternatively, labelled polypeptides of the invention can be used to detect the presence of antibodies to RSP-1 or RSP-2 in a biological sample. For a review of the general procedures in diagnostic immunoassays, see Basic and Clinical Immunology 7th Edition (D. Stites and A. Terr ed.) 1991.

In addition, modified polypeptides, antibodies or other compounds capable of inhibiting the interaction between RSP-1 and RSP-2 and erythrocytes can be assayed for biological activity. For instance, polypeptides can be recombinantly expressed on the surface of cells and the ability of the cells to bind erythrocytes can be measured as described below. Alternatively, peptides or antibodies can tested for the ability to inhibit binding between erythrocytes and Plasmodium and/or RSP-1 and/or RSP-2.

Cell-free assays can also be used to measure binding of RSP-1 or RSP-2 polypeptides, for example, the sample can be immobilized on a solid surface and binding of labeled RSP-1 or RSP-2 can be determined. Many assay formats employ labeled assay components. The labeling systems can be in a variety of forms. The label (detectable moiety) may be coupled directly or indirectly to the desired component of the assay according to methods well known in the art. A wide variety of labels may be used. The component may be labeled by any one of several methods. The most common method of detection is the use of autoradiography with $^{3}H$, $^{125}I$, $^{35}S$, $^{14}C$, or $^{32}P$ labeled compounds or the like. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation.

In the case of the use nucleic acids for diagnostic purposes, standard nucleic hybridization techniques can be used to detect the presence of the genes identified here, RSP-1 and/or RSP-2. If desired, nucleic acids in the sample may first be amplified using standard procedures such as PCR. Diagnostic kits comprising the appropriate primers and probes can also be prepared.

RSP-1 and RSP-2 are usefull in therapeutic and prophylactic applications for the treatment of malaria. Pharmaceutical compositions of the invention are suitable for use in a variety of drug delivery systems. Suitable formulations for use in the present invention are found in Remington's Pharmaceutical Sciences, Mack Publishing Company, Philadelphia, Pa., 17th ed. (1985). For a brief review of methods for drug delivery, see, Langer, Science 249:1527-1533 (1990). The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmtic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount administered to the patient will vary depending upon what is being administered, the state of the patient and the manner of administration. In therapeutic applications, compositions are administered to a patient already suffering from malaria in an amount sufficient to inhibit spread of the parasite through erythrocytes and thus cure or at least partially arrest the symptoms of the disease and its complications. An amount adequate to accomplish this is defined as "therapeutically effective dose." Amounts effective for this use will depend on the severity of the disease, the particular composition, and the weight and general state of the patient.

Alternatively, the polypeptides of the invention can be used prophylactically as vaccines. The vaccines of the invention contain as an active ingredient an immunogenically effective amount of the binding domain polypeptide or of a recombinant virus as described herein. The immune response may include the generation of antibodies; activation of cytotoxic T lymphocytes (CTL) against cells presenting peptides derived from RSP-1 and/or RSP-2, or other mechanisms well known in the art. See e.g. Paul Fundamental Immunology Second Edition published by Raven press New York (incorporated herein by reference) for a description of immune response. Useful carriers are well known in the art, and include, for example, thyroglobulin, albumins such as human serum albumin, tetanus toxoid, polyamino acids such as poly(D-lysine: D-glutarnic acid), influenza, hepatitis B virus core protein, hepatitis B virus recombinant vaccine. The vaccines can also contain a physiologically tolerable (acceptable) diluent such as water, phosphate buffered saline, or saline, and farther typically include an adjuvant. Adjuvants such as incomplete Freund's adjuvant, aluminum phosphate, aluminum hydroxide, or alum are materials well known in the art. The DNA or RNA encoding RSP-1 or RSP-2 may be introduced into patients to obtain an immune response to the polypeptides which the polynucleotide encodes.

Vaccine compositions containing the proteins, nucleic acids or viruses of the invention are administered to a patient to elicit a protective immune response against the polypeptide. A "protective immune response" is one which prevents or inhibits the spread of the parasite through erythrocytes and thus at least partially prevent the symptoms of the disease and its complications. An amount sufficient to accomplish this is defined as an "immunogenically effective dose." Amounts effective for this use will depend on the composition, the manner of administration, the weight and general state of health of the patient.

After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters.

Having generally described this invention, a further understanding can be obtained by reference to certain specific examples which are provided herein for purposes of illustration only, and are not intended to be limiting unless otherwise specified.

EXAMPLES

Parasites

The following parasite isolates were used in this study: Palo-Alto (FUP)1[13], IPL/BRE1[14], FCR3 subpopulations panned on CSA, CD36 and ICAM-1[15], two isolates desequestered using soluble CSA from infected human placentas ($42^{CSA}$ and $939^{CSA3}$) and a CSA-selected population of a field isolate collected from the peripheral bloodstream ($A53^{CSA}$). The IE were cultured in RPMI 1640 containing bicarbonate, glutamine, 0.2% glucose, 50 μM hypoxanthine, 10 g/ml gentamicin and 10% human $AB^+$ serum, containing $O^+$ eythrocytes, at 37° C. in a humidified atmosphere containing 5% $O_2$, 5% $CO_2$ and 90% $N_2$. IE cultures were synchronized by selecting ring-stage parasites using multiple 5% sorbitol treatments until the parasites reinvaded erythrocytes within 4h.

Selection by Panning

Subpopulations of the Palo-Alto (FUP)1, (PA), IPL/BRE1 (BRE1), FCR3 strains and of the A53 isolate were selected by three successive pannings of mature stage IE on cellular CSA as previously described[15], using SBEC 17[16]. In addition, subpopulations of PA and FCR3 were selected by three successive pannings of mature stage IE on cellular CD36 or ICAM-1, using chondroitinated SBEC C2 and 3A[15]. Highly synchronsized ring-stage IE cultures were panned on SBEC 1D expressing CSA, CD36 and ICAM-1, as previously described. The cells were washed extensively to remove non-cytoadherent IE and were then incubated in culture medium for 24 hours to allow ring-stage IE to mature. RBC were added and the cultures grown as previously described.

Cytoadhesion and Cytoadhesion Inhibition Assays

Gelatin-enriched preparations of mature-stage IE were resuspended at a concentration of $5 \times 10^6$ IE/ml in cytoadhesion medium at pH 6.8. Cytoadhesion microassays were then performed on 12-well IFA slides (Institut Pasteur, Paris) as previously desribed[15].

Ring-stage cytoadhesion assays were performed with endothelial cells as described above and with placental cryosections as previously described[11], with 1 to 10% parasitaemia (a $1 \times 10^7$ IE/ml suspension).

For cytoadhesion inhibition assays, the IE were incubated with SBEC in the presence of 2.5 μg/ml thrombospondin, 0.1 mg/ml soluble CSA, dermatan sulphate (CSB), chondroitin-6-sulphate (CSC), keratin sulphate (Ker), byaluronic acid (HA), heparin (Hep) (Fluka, France), or with SBEC previously incubated for 1 hour at 37° C. with 1 U/ml Case ABC (Fluka, France), 1 to 10 U/ml heparinase III (Hepase III (Sigma, France) or 5 μg/ml anti-CD36 FA6-152 Mab (gift from Dr. Edelman). Inhibition assays were also carried out in the presence of sera obtained from Senegalese and Cameroonian patients living in areas of endemic malaria. The sera were obtained from primigravida and multigravida women, a male adult and a child, absorbed onto $O^+$ human blood and SBEC ID, and tested at a dilution of 1/20. The results were compared to those for cytoadhesion in the presence of a 1/20 dilution of a pool of control sera from volunteers who had never contacted malaria.

The protease sensitivity of ring-stage IE cytoadhesion was analyzed using 5 μl of packed $PA^{CSA}$ IE (8 hours post-invasion). IE were incubated with 10 or 100 μg/ml of trypsin TPCK (Signa) or 100 g/ml of -chymotrypsin TLCK (Sigma) for 30 minutes at 37° C. The digestion was topped by adding culture medium containing 10% human plasma. The cells were then washed in cytoadhesion medium and allowed to cytoadhere to SBEC ID, as previously described, using untreated $PA^{CSA}$ as a control.

Surface Immunolabeling of IE

100 μl of a pool of 5 sera from Senegalese and Cameroonian patients liting in an area of endemic malaria was adsorbed onto 30 l of $O^+$ human blood, once at 37° C. and once at room temperature. 5 μm of highly synchronized ring- or trophozoite-stage $PA^{CSA}$ IE were incubated on ice for 45 minutes with 100 μl of the pool of sera diluted 1/10 in cytoadhesion medium. The IE were washed three times in cytoadhesion medium and incubated for 45 minutes on ice with FITC-conjugated anti-human IgG (Sigma, F-6380). After a final wash, the IE were observed by EPR microscopy (CELLscan, Scanalytics, Billerica, MA[17]).

Surface Iodination and Metabolic Labeling of IE

Synchronized mature-stage IE previously selected on CSA and CD36 by the receptor panning procedure[18] were enriched to >75% by the gelatin technique and hen diluted with fresh aythrocyes to obtain approximately 20% ring-stage forms at the next cycle. Surface iodination was performed using the lactoperoxidase method[7], 7, 14, 21 and 32 hours after re-invasion. Metabolic labeling was performed by adding 2 mCi $^{35}$S-methionine to a 5 ml culture flask at the late schizont-stage. The culture was stopped 14 hours after re-invasion. Sequential extraction with 1% Triton X-100 then 2% SDS was carried out, followed by protease treatment (TPCK-treated trypsin and -achmotrypsin TLCK (Sigma, Lt. Louis) as previously described). Samples iodinated or metabolically labeled were separated on a 5%-17.5% gradient acrylamide gel, which was then dried and placed against Kodak Bio Max MS1 film. Prestained protein markers were purchased from Life Technologies, Gaithersburg, Md. and New England BioLabs Inc., Beverly, Mass.

Statistical Analysis

The results of IE adhesion, cytoadhesion and cytoadhesion inhibition assays are expressed as means±SE. The Mann-Whitney test was used to evaluate the statistical significance of data from cytoadhesion inhibition assays and to compare cytoadhesion levels.

TABLE 1

Cytoadhesion of IE$_S$ $^{CSA}$ to Saimiri brain endothelial cells ID IE$^{CSA}$ cytoadhesion during the first 2 hours of the cycle

| 1E | 4H | 8H | 12H | 16 | 20H |
|---|---|---|---|---|---|
| Laboratory strains | | | | | |
| PA$^{CSA}$ | 64 ± 42 | 73 ± 59 | 122 ± 177 | | |
| Bre$^{CSA}$ | 35 ± 15 | 38 ± 19 | 128 ± 59 | | |
| FCR$^{CSA}$ | 278 ± 210 | 237 ± 124 | 86 ± 21 | | |
| Peripheral Blood | | | | | |
| ioslate | | | | | |
| A53$^{CSA}$ | 46 ± 29 | 32 ± 21 | 53 ± 33 | | |
| Placental Isolates | | | | | |
| 42$^{CSA}$ | 29 ± 26 | 28 ± 12 | 51 ± 37 | | |
| 939$^{CSA}$ | 47 ± 38 | 57 ± 50 | 71 ± 37 | | |

Data are the mean number (±SD) of cytoadherent IE/mm$^2$ of SBEc ID monolayer (mean of quadruplicate spots). Nd: not done. The shadowed values correspond to PfEMP1-mediated cytoadhesion.

Results

Figures 1C, 1D:
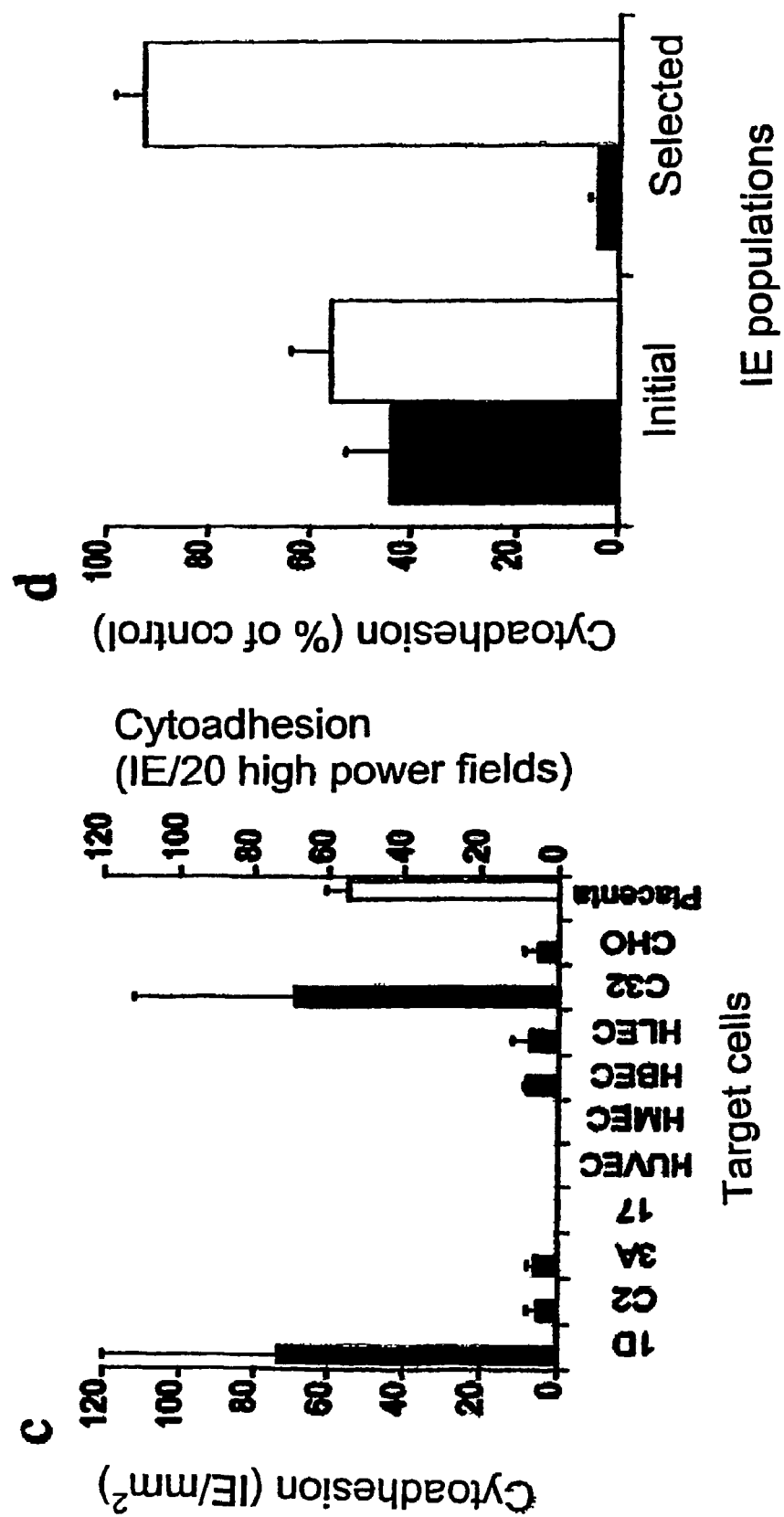

The peripheral blood of pregnant women infection with *P. falciparum* may be devoid of circulating ring-stage IE[4,5] or contain IE with little or no CSA binding phenotype[2,3] despite the massive binding of IE to placenta CSA. This led us to investigate whether ring-stage IE from pregnant women are able to avoid circulating in the peripheral blood. We tested ring-stage adhesion to placenta and various cell types. Highly synchronized young ring-stage IE of *P. falciparum* isolate Palo-Alto (FUP)[1], prepared in vitro and selected for binding to CSA (PA$^{CSA}$), adhered to syncytiotrophoblasts in placenta cryosections and monolayers of cultured Saimiri brain endothelial cells (SBEC) (FIGS. 1A, B and C). Binding was observed immediately after merozoite reinvasion and continued throughout the ring-stage cycle (Table 1). There was extensive specific binding of ring-stage IE to SBEC ID and melanoma C32 cells (approx. 70 IE/mm$^2$). The level of binding to human brain endothelial cells (HBEC), human lung endothelial cells (HLEC) and CHO cells was low but significant ($\geq$5 IE/mm$^2$ of cell monolayer) (FIG. 1C). Finally, no ring-stage IE cytoadhesion to human umbilical vein endothelial cells (HUVEC, primo explants) and human dermal endothelial cells (HMEC-1) was detected. We investigated additional genetically different CSA-binding isolates: one from the peripheral blood of a child (A53$^{CSA}$), two placental isolates, 939$^{CSA}$ and 42$^{CSA}$, and two isolates cultured in vitro (FCR3$^{CSA}$ and Bre1$^{CSA}$). The results obtained confirmed that ring-stage IE bound to endothelial cells (Table 1).

Ring-stage adhesion was not detected in PA and FCR3 parasites selected for binding at the trophozoite stage to CD36 or ICAM-1 (<1 bound IE/mm$^2$ of SBEC 1D). These data suggest that the CSA-binding phenotype is connected to ring-stage adhesion by an unknown mechanism. We investigaged this by mixing equal numbers of highly synchronized ring-stage IE (8 hours after re-invasion) selected for bind to CSA and CD36 and allowing them to bind to a monolayer of SBEC 1D. Bound ring-stage IE were cultured and their phenotypes were assessed at the trophozoite stage by measuring the sensitivity to phenotype-specific inhibitors (soluble CSA mAb directed against CD 36) of adhesion. Almost all trophozoite binding was CSA-dependent whereas the noon-selected IE combinations were inhibited similarly by both inhibitors (FIG. 1D). Similar selection was observed for the binding for mature IE to CSA if a mixture of IE subpopulations binding to CSA and ICAM-1 was tested (data not shown). Therefore, for the three phenotypes tested, the ability to cytoadhere before the trophozoite stage was strictly linked to the CSA-binding phenotype of mature IE.

Figure 2A:
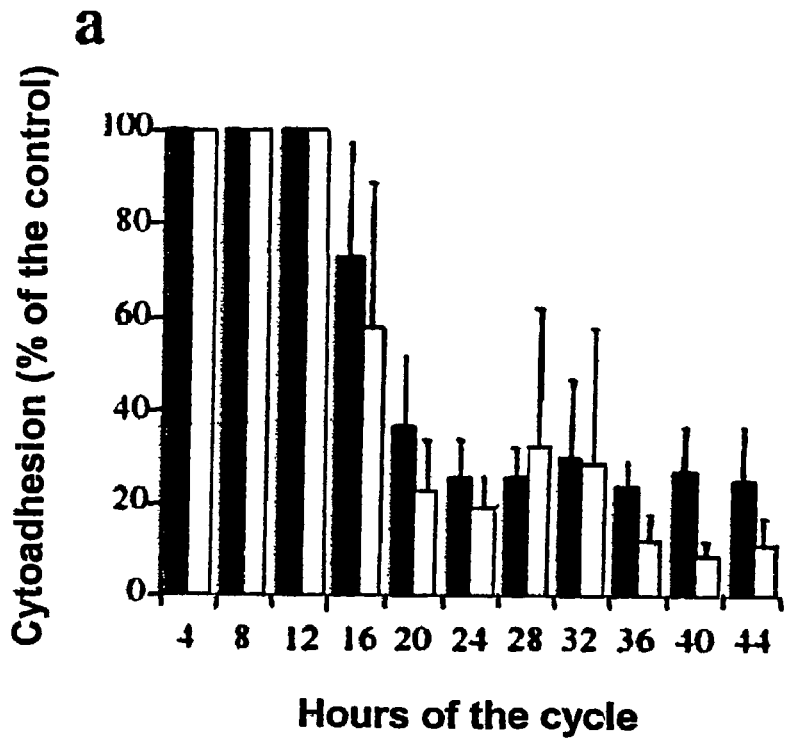
FIG. 2: Cytoadhesion throughout the blood-stage cycle is mediated by a switch in adhesion phenotype. (A) Determination of the inhibitory activity of CSA (■) and chondroitinase ABC (□) on the cytoadhesion of SBEC 1D of highly synchronized $PA^{CSA}$ IE, every 4 hours throughout the cycle. (B) Cytoaadhesion of ring-stage $PA^{CSA}$ IE to SBEC ID 8 hours post-invasion in the presence of dermatan-sulphate (CSB), chondroitin-6-sulphate (CSC), keratan sulphate (Ker), hyalwonic acid (HA), heparin (Hep), or after treatment of the target cells with chondroitinase ABC (Case ABC) and B (Case B), hyaluronaste lyase (H Lyase) and heparinase II (Hepase).
Figure 2B:
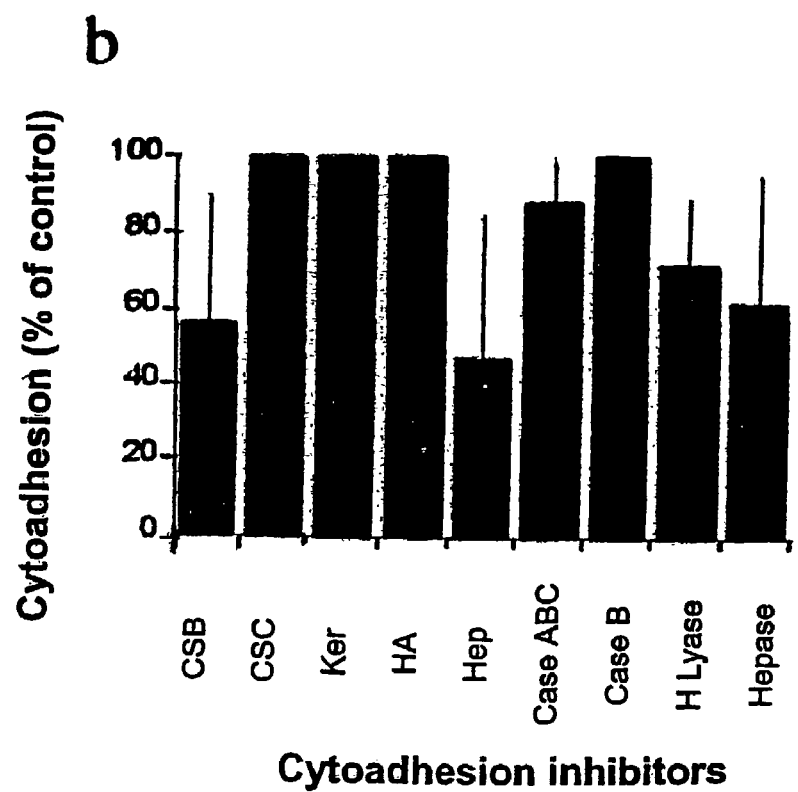

To identify the host receptor involved in ring-stage adhesion, we tested the inhibitory activity of CSA throughout the cycle. We observed that ring-stage IE$^{CSA}$ cytoadhesion was insensitive to 0.1 mg.ml of CSA and to the prior treating of the target cells with 1 U/ml of chondroitinase ABC (Case ABC) until the 16th hour after invasion (FIG. 2A). At this time, with the beginning of knob formation and surface expression of the var$^{CSA}$ gene, the inhibitory effects on binding of CSA and Case ABC were first seen. Inhibition was maximal at hour 24. Thus, all IE$^{CSA}$ cytoadhere throughout the blood-stage cycle, switching from CSA-independent receptor interaction to a CSA-dependent phenotype 16 hours after invasion. We tested the possible involvement of various mature-stage IE adhesion receptors. Thrombospondin had no effect on IE binding to SBEC 1D (data not shown). Transfected CHO 745 (CSA$^-$) expressing CD36, ICAM-1, VCAM or E-selectin at their surface showed non-specific cytoadhesion of ring-stage IE similar to that of the CHO-745 control cells ($\leq$2 bound IEs/mm$^2$). We also investigated the possible inhibitory effects of various glycosaminoglycans and their corresponding enzymes (FIG. 2B). The inhibition obtained with dermatan-sulphate (CSB) was not specific as Case ABC and B had no significant inhibitory activity. Hyaluronic acid had no activity whereas hyaluronate lyase had a low level of inhibitory activity, probably due to its secondary capacity to digest heparin and heparan sulphates. Heparin (100 m/ml) and heparinase gave about 50% inhibition, SBEC ID do not express heparin at their surface. Instead, they express heparan sulphate proteoglycans[6], and it is probably by completion with or digestion of SBEC 1D heparan sulphate that heparin and heparinase II partially inhibit ring-stage cytoadhesion. We are currently purifying SBEC 1D heparan sulphates to test their inhibition of ring-stage IE$^{CSA}$ cytoadhesion.

Figures 3A, 3B:
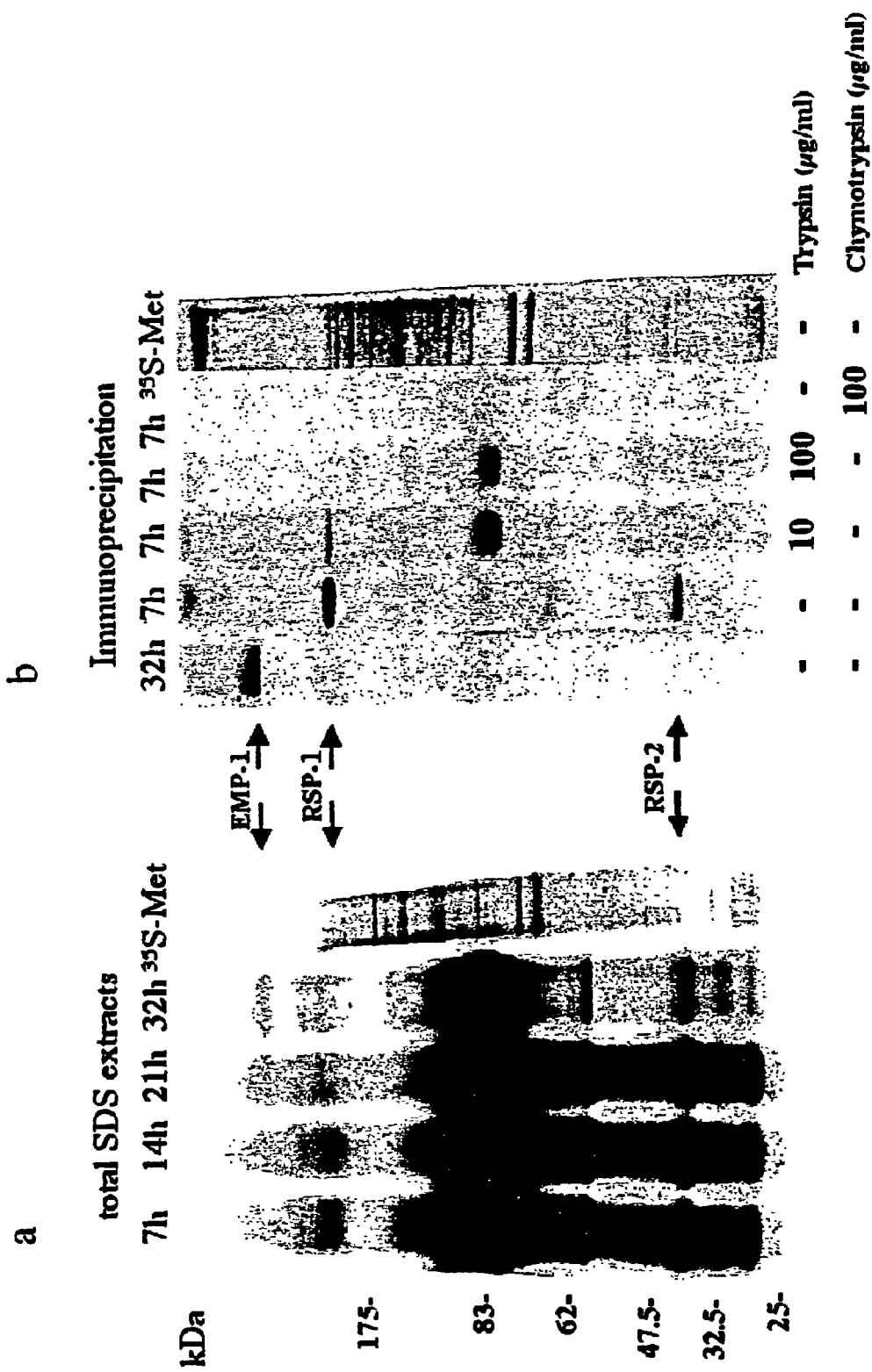
FIG. 3: Adhesive ring-stage IE express novel ring staespecific surface molecules that are targets o the immune response. (A) Identification of a high-molecular weight $^{125}$I-labeled surface antigen on a ring-stage IE. The separation of SDS extracts of the iodinated surface $FCR3^{CSA}$ at various time points after merozoite re-invasion (7, 14, 21 and 32 hours) is shown. A single labeled band of approximately 200 kDa (RSP-1) is detected from the early ring (7 hour) to early trophozoite stages (21 hour). A second labeled band of approximately 400 kDa appears at 14 hours and is detected until he end of the cycle. $^{35}$S-labeled ring-stage IE extracts show a 200 kDa band that co-migrates with RSP-1. The 200 and 400 kDa bands are not seen in control erythrocytes (data not shown). (B) A pool of immune sera from pregnant women (Cameroon) immunoprecipitated two major protease-sensitive proteins of approximately 200 and 40 kDa. Later in the life cycle, the $var^{CSA}$ molecule (400 kDa) is immunopurified. Lane 1: trophozoite stage 32 hours post-infection) followed by $^{125}$I-labeled young ring-stage (lane 2) and trypsin (tryp) treatment before immunoprecipitation: 10 μg/ml trypsin (lane 3), 100 μg/ml trypsin (lane 4) and 100 μg/ml α-chymotrypsin (chymo; lane 5). $^{35}$S-methionine labeled ring-stage IE SDS extract immunoprecipated with the serum pool (lane 6). (C) Sensitivity of cytoadhesion to the treatment ring-stage IE with different concentrations of trypsin or α-chmotrypsi. (D) Immunolabeling of ring-stage (R) and trophozoite-stage (T) $PA^{CSA}$ IE with a pool of 5 sera from Senegalese and Cameroonian patients living in areas of endemic malaria. Antibodies at the surface of the IE were detected with an FTFC-conjugated anti-human IgG and were observed by EPR microscopy (CELLscan). (E) Cytoadhesion inhibition by sera obtained from a primigravida (1), and multigravida (25 and 46) women, a child (61) and a male adult (1613). The percentage cytoadhesion was obtained by comparing the binding obtained in the presence of each serum with a control carried out with a pool of sera from volunteers who had never contracted malaria.
Figure 3D:
Figure 3C:
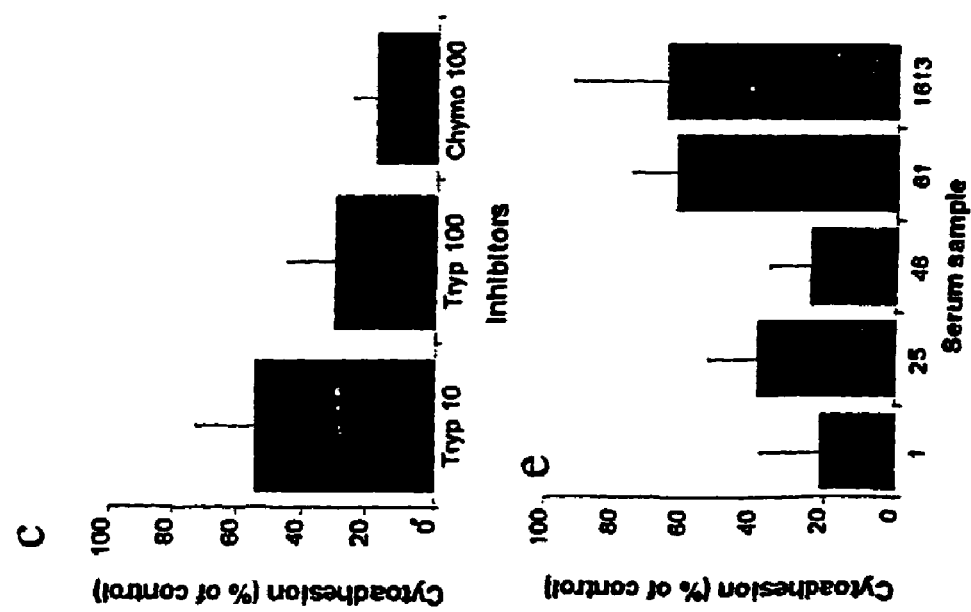

As ring-stage IE$^{CSA}$ adhesion is not mediated by CSA, we thought it likely that a novel parasite surface molecule mediated binding to endothelial cells and syncytiotrophoblasts in early blood stage parasites. Surface iodination of FCR3$^{CSA}$ ring-stage IE identified a molecule of approximately 200 kDa that was absent from control erythrocytes and is referred to here as "ring surface protein-1" (RSP-1) (FIG. 3). We immunoprecipitated surface-iodinated ring-stage IE extracts using a pool of serum from ultigravida women from Cameroon. The sera used recognized the 200 kDa molecule and a second molecule of approximately 40 kDa, termed RSP-2. RSP-2 was not detectable in total parasite extracts because it co-migrates with a band strongly labeled in uninfected erythrocytes. Parasite proteins identical in size to RSP-1 and RSP-2 were found in S-methionine labeled protein extracts from ring-stage IE. RSP-1 and RSP-2 were efficiently extracted in 2% SDS and were degraded by trypsin (100 μm/ml) or -chymotrypsin (100 g/ml) treatment (FIGS. 3A and B, and data not shown). Ring-stage 1E adhesion was substantially inhibited at a protease concentration of 100 μg/ml (FIG. 3C), consistent with the involvement of RSP-1 and RSP-2 in the adhesion process. Both molecules were detected at the surface of young ring-stage IE but neither was present in mature trophozoites. In trophozoite IE, a large molecule, approximately 400 kDa in size, was detected at the IE surface (between 14 and 21 h post-invasion, FIGS. 3A and B) at a time coinciding with the switch in adhesive phenotype. The 400 kDa molecule of $FCR3^{CSA}$ IE was identified in a previous study as the var gene product, which mediates the adhesion of mature forms to CSA. The RPS-1, RPS-2 and $var^{CSA}$ molecule are naturally immunogenic and were efficiently immunoprecipitated by 8 sera from pregnant women (FIG. 3B and data not shown). These sera react with the surface of ring-stage and trophozoite-stage IE (FIG. 3E). Sera from malaria patients from Cameroon/Senegal (pregnant women, male adults and children) blocked the cytoadhesion of ring-stage IE to endothelial cells (FIG. 3F).

Our work challenges current views concerning the blood-stage biology of P. falciparum. It is generally accepted that ring-stage IE circulate in the blood and that adhesive properties become evident with the expression of the PfEMP1 molecule at the IE surface approximately 14 to 16 hours after invasion. Here we describe for the first time the specific adhesion of young ring IE to endothelial cells from critical target organs such as the brain and lung and to syncytiotrophoblasts. The differences between placental and peripheral blood parasitaemia and phenotype distribution observed in infected pregnant women can be accounted for by our findings. We suggest that the adhesion of ring-stage IE to placenta syncytiotrphoblasts precedes the CSA-binding of mature-stage IE, leading to a cryptic, or at least partially cryptic, life cycle of parasites with this adhesive phenotype. Evidence that ring-stage IE may cytoadhere in patients other than pregnant women comes from a recent study on sequestration of P. falciparum in the human brain[8]. All developmental stages were observed in brain vessels of patients dying from cerebral malaria. Some vessels clearly contained large numbers of ring-stage IE but the nature of the interaction is unknown. As CSA is present in the brain microvasulature[9-11], IE subpopulations may adhere to the same host cell throughout the blood stage cycle. Clearly, the absence or under-representation of specific virulent adhesive phenotypes in the bloodstream has a major impact on clinical studies based on peripheral blood-stage parasites. The role of ring-stage adhesion in tissue tropism should also be investigated. It is tempting to speculate that the massive accumulation of CSA-binding parasites observed in the placenta, for example, is due to the initial binding of rings.

The level of ring-stage adhesion to endothelial cells is markedly lower than that of trophozoite binding. This may be due to differences in the strength of the interaction between ligand and receptor pairs or to there being fewer ring-stage adhesion receptors than CSA molecules. Prelimary data obtained in flow-based assays, indicate an order to magnitude difference in strength of interaction between the ring and mature stages. Ring-stage adhesion is presumably maximal in the placenta, where blood flow is much lower than in other vascular beds.

The switch between two different adhesive phenotypes during the 48-hour blood-stage cycle is an entirely new phenomenon in the biology of P. falciparum. The expression pattern of IE surface molecules throughout the blood-stage cycle coincides with the observed change in adhesive phenotype, thus suggesting a role for RSP-1 and/or RSP-2 in ring-stage IE adhesion. In parasite that do not present ring-stage adhesion (CD36 phenotype), surface molecules with molecular masses similar to those of RSP-1 and RSP-2 were detected (data not shown). It is unclear whether RSP-1 and RSP-2 are members of a ene family or if phenotype-specific post-translational modifications of IE surface molecules[12] are responsible for the differences in adhesive features of rings.

Finally, the novel ring-stage IE surface molecules RSP-1 and RSP-2 are nature targets of the antibody-mediated immune response capable of blocking ring-stage adhesion. These antigens were therefore potential vaccine candidates that could reduce the severity of this major disease.

Obviously, numerous modifications and variations on the present invention are possible in light of the above teachings. It is therefore to be understood that within the scope of the appended claims, the invention may be practiced otherwise than as specifically described herein.

REFERENCES

1. Miller, L. H., Good, M. F. & Milton, G. Malaria pathogenesis. Science 264, 1878-1883 (1994).

2. Fried, M. & Duffy, P. E. Adherence of Plasmodium falciparum to chondroitin sulfate A in the human placenta. Science 272, 1502-1504 (1996).

3. Gysin, J., Pouvelle, B. Fievet, N., Schert, A & Lepolard, C. Ex vivo desequestration of Plasmodium falciparum-infected erythrocytes from human placenta by chondroitin sulfate A. Infect. Immun. 67, 6596-6602 (1999).

4. Watkinson, M. & Rushton, D. J. Plasmodial pigmentation of placenta and outcome of pregnancy in West African moths. Brit. Med. J. 287, 251-254 (1983).

5. Matteelli, A. et al, Malaria and anaemia in pregnant women in urban Zanzibar, Tanzania Ann. Trop. Med. Parasitol. 88, 475-483 (1994).

6. Fusai, T. et al, Characterisation of the chondroitin sulphate of Saimiri brain microvascular endothelial cells involved in P. falciparum cytoadhesion. Mol. Biochem. Parasitol., in press (2000).

7. Buffet, P. A. et al. Plasmodium falciparum domain mediating adhesion to chondroitin sulfate A: A receptor for human placental infection. Proc. Natl. Acad. Sci. U.S.A. 96, 12743-12748 (1999).

8. Silamut, K. et al. A quantitative analysis of the microvascular sequestration of malaria parasites in the human brain. Am. J. Pathol. 155, 395-410 (1999).

9. Boffa, M. C., Jackman, R. W., Peyri, N. & George, B. Thrombomodulin in the central nervous system. Nouv. Rev. Fr. Hematol. 33, 423-429 (1991).

10. Wong, V. L., Hofman, F. M. Ishii, H. & Fisher, M. Regional distribution of thrombomodulin in human brain. Brain Res. 556, 105 (1991).

11. Gysin, J., Pouvelle, B., Le Tonqueze, M., Edelman, L. & Boffa, M. C., Chondroitin sulfate of thrombomodulin is an adhesion receptor for Plasmodium falciparum-infected erytirocyics. Mol. Biochem. Parasitol. 88, 267-271 (1997).

12. Fernandez, V. Hommel, M. chen, Q., Hagblom, P. & Wahlgren, M. Small, clonally variant antigens expressed on the surface of the *Plasmodium falciparum*-infected erytlrocyte are encoded by the rif gene family and are the target of human immune responses. J. Exp. Med. 190, 1393-1404 (1999).

13. Gysin, J. & Fandeur, T. *Saimiri sciurues* (Karyotype 14-7) an alternative experimental model of *Plasmodium failciparum* infection. Am. J. Trop Med. Hyg. 32, 461-467 (1983).

14. Robert, C. et al Chondroitin-4-sulphate (proteoglycan), a receptor for *Plasmodium falciparum*-infected erythrocyte adherence on brain microvascular endothelial cells. Res. Immunol. 146, 383-393 (1995).

15. Pouvelle, B. Fusai, T. Lepolard, C. & Gysin, J. biological and biochemical characteistics of cytoadhesion of *Plasmodium falciparum*-infected eryhrocytes to chondroitin-4-sulfate. Infect. Immun. 66, 4950-4956 (1998).

16. Gay, F. et al, Isolation and characterization of brain microvascular endothelial cells from Saimiri monkeys. An in vitro model for sequestration of *Plasmodium falciparum*-infected erythrocytes. J. Immunol. Meth. 184, 15-28 (1995).

17. Carter, K. C. et al. A three-dimensional view of precursor messenger RNA metabolism within the mammalian nucleus. Science 259, 1330-1335 (1993).

18. Scherf, A. et al. Antigenic variation in malaria: in situ switching, relaxed and mutally exclusive transcription of var genes during intra-erythrocytic development in *Plasmodium falciparum*. Embo J. 17, 5418-5426 (1998).

The invention claimed is:

1. A composition comprising an isolated ring surface protein-1 (RSP-1) from *P. falciparum* during ring-stage infection of erythrocytes and a pharmaceutical acceptable carrier, wherein the RSP-1 has MW of about 200 kDa as determined by SDS-PAGE.

2. The composition of claim 1, which is an immunogenic composition.

3. The composition of claim 2, which further comprises an adjuvant.

* * * * *